United States Patent [19]

Hochmair et al.

[11] Patent Number: 5,070,535
[45] Date of Patent: Dec. 3, 1991

[54] TRANSCUTANEOUS POWER AND SIGNAL TRANSMISSION SYSTEM AND METHODS FOR INCREASED SIGNAL TRANSMISSION EFFICIENCY

[76] Inventors: Ingeborg J. Hochmair; Erwin S. Hochmair, both of A-1130 Wien Jaunerstrasse 27, Vienna, Austria

[21] Appl. No.: 9,565

[22] Filed: Jan. 30, 1987

Related U.S. Application Data

[63] Continuation of Ser. No. 714,023, Mar. 20, 1985, abandoned.

[51] Int. Cl.$^5$ ............................................... H04B 5/00
[52] U.S. Cl. .................................. 455/41; 128/420.6; 128/903; 381/68
[58] Field of Search ............ 455/41; 128/903, 419 PT, 128/420.6; 379/55; 381/68, 79

[56] References Cited

U.S. PATENT DOCUMENTS

| | | | |
|---|---|---|---|
| 3,078,348 | 2/1963 | McIntosh | 455/41 |
| 4,281,664 | 8/1981 | Duggan | 128/903 |
| 4,357,497 | 11/1982 | Hochmair et al. | 179/107 E |
| 4,441,210 | 4/1984 | Hochmair et al. | 455/41 |
| 4,586,508 | 5/1986 | Batina et al. | 128/903 |
| 4,654,880 | 3/1987 | Sontag | 455/41 |

Primary Examiner—Curtis Kuntz
Attorney, Agent, or Firm—Flehr, Hohbach, Test, Albritton & Herbert

[57] ABSTRACT

A transcutaneous signal transmission system having coupling coil alignment tolerance and increased coupling efficiency includes an external transmitter and first tuned circuit including a first coupling coil and an implantable receiver and second tuned circuit including a second coupling coil. The first and second tuned circuits are stagger tuned whereby closer spacing of the coupling coils is permitted in achieving optimum coupling.

4 Claims, 2 Drawing Sheets

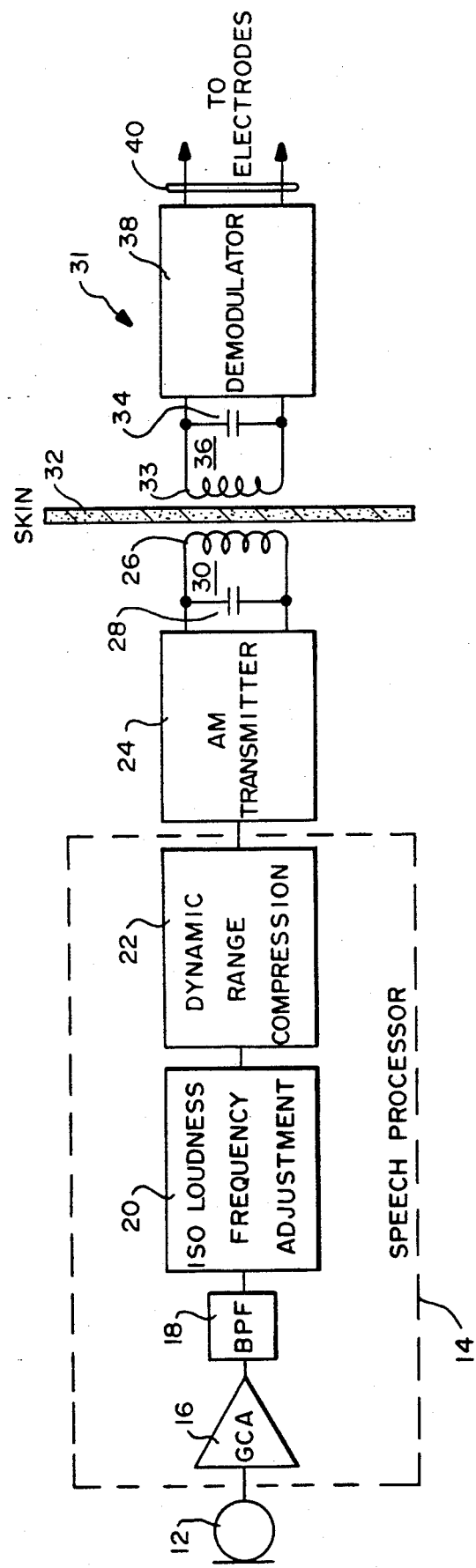
FIG.—1

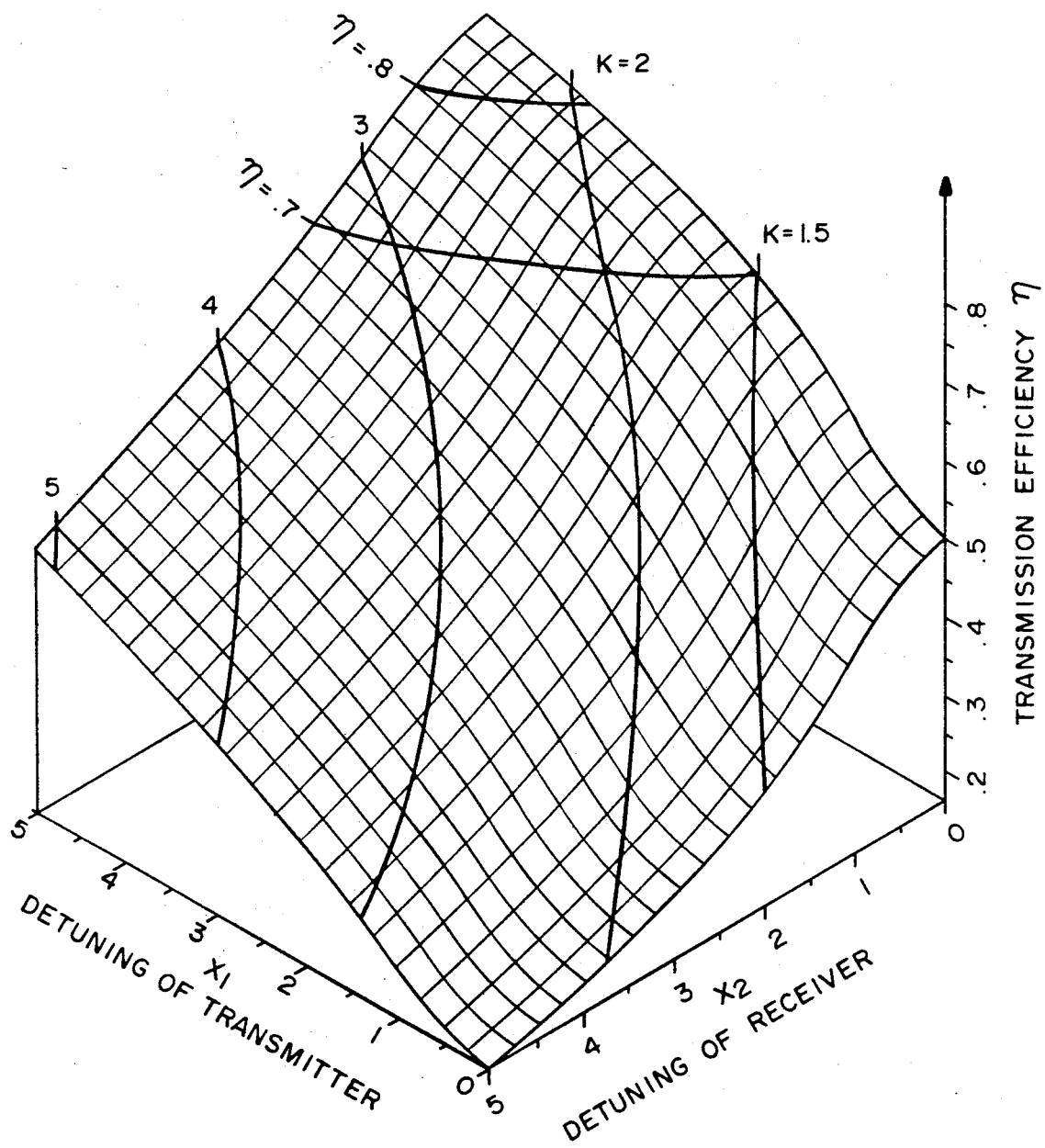
FIG.—2

TRANSCUTANEOUS POWER AND SIGNAL TRANSMISSION SYSTEM AND METHODS FOR INCREASED SIGNAL TRANSMISSION EFFICIENCY

This is a continuation of application Ser. No. 714,023 filed Mar. 20, 1985 now abandoned.

This invention relates generally to systems for transmitting electrical signals into the body of a patient, and more particularly the invention relates to the transmission of signals to a receiver which is implanted in the body.

Transcutaneous signal transmission systems are known and widely utilized for neural and muscle stimulation. Such systems are generally preferred over other transmission systems such as the use of implanted batteries or the use of direct percutaneous wiring. Typically, a transmitter transmits a modulated signal to an implanted receiver via two inductively coupled coils. The coils are part of tuned circuits which can cooperatively function as a bandpass filter. Our U.S. Pat. No. 4,284,856 and U.S. Pat. No. 4,357,497 disclose auditory stimulation apparatus in which inductive coupled coils are utilized in transcutaneous signal transmission.

Heretofore, inductive transmission systems have been designed for optimum efficiency with a consequential dependence of induced voltage in the implanted coil on exact positioning of the transmitter coil. Thus, in applications such as auditory stimulation where a precise output signal is necessary, the inductive transmission system has limitations in effectiveness.

Our U.S. Pat. No. 4,441,210 discloses a method and apparatus which allows a tolerance in coil alignment for optimum signal transmission. The transmitter and receiver coils are atuned to the frequency of the transmission signal, and critical coupling is achieved between the coils. Critical coupling is realized by adjusting the spacing of the coils whereby the output impedance of the transmitter decreases to one-half of the output impedance of the transmitter with no coupling. Spacing between the coils cannot decrease below a predetermined limit because the coils would then become overcoupled and resulting in a drop in signal. Practically speaking, the alignment tolerance realized with critical coupling is offset by a limit in transmission efficiency of about 50%.

An object of the present invention is a method and means of maintaining coil alignment tolerance while increasing the efficiency in signal transmission.

A feature of the invention is the use of transmitter and receiver tuned circuits which are not tuned to the same frequency.

Briefly, the transmission system in accordance with the invention includes a transmitter in which audio signals modulate a carrier signal at an RF frequency. The modulated carrier signal is inductively coupled from a transmitter tuned circuit to a receiver tuned circuit. The two tuned circuits are stagger tuned whereby closer spacing of the coupling coils is required for optimum signal coupling. Importantly, the closer spacing of the coils for optimum coupling permits an increase in signal transmission efficiency to 90% or more.

In a preferred embodiment, the receiver circuit is tuned to the carrier signal frequency, and the transmitter circuit is detuned to increase coupling of the two tuned circuits at optimum coupling. It has been found that signal transmission efficiency increases substantially (i.e. from 50% to 90% or more) with only a small decrease in alignment tolerance.

The invention and objects and features thereof will be more readily apparent from the following detailed description and appended claims when taken with the drawing, in which:

FIG. 1 is a functional block diagram of an auditory stimulation system in accordance with one embodiment of the invention.

FIG. 2 is a plot illustrating signal transmission efficiency as a function of transmitter and receiver detuning from the transmission frequency.

Referring now to the drawings, FIG. 1 is a functional block diagram of auditory stimulation apparatus in accordance with one embodiment of the invention. Similar apparatus is disclosed in U.S. Pat. No. 4,441,210, supra. A microphone 12 has its output applied to a speech processor electronics shown as being enclosed by the broken line box 14. Included in the speech processor channel is a gain control amplifier 16 which receives as its input the electrical output from the microphone 12, and the output from the gain control amplifier 16 is applied through a bandpass filter 18 to an isoloudness frequency adjustment circuit 20. Circuit 20 is a frequency dependent network which compensates for the fact that the stimulated current for a given loudness is frequency dependent. The speech processor electronics 14 further includes a dynamic range compression circuit 22 which may either precede or follow the isoloudness frequency adjustment circuit 20.

The output of the speech processor 14 is arranged to modulate the output of an RF oscillator in the AM transmitter module 24. The modulated output from the transmitter is applied across a transmitting coil 26 and a capacitor 28, these last mentioned two components being designed to cooperate as a tuned circuit 30.

The implant unit 31 is shown to the right of the skin interface 32 and includes the receiver coil 33 which has a capacitor 34 connected in parallel with it. The parallel combination of the receiving coil 33 and the capacitor 34 forms a tuned receiver circuit 36. The output from the tuned receiver circuit is coupled as an input to a diode demodulator network 38 which functions in a conventional fashion to remove the modulation envelope from the RF carrier. The output of the diode demodulator is applied via the leads 40 to electrodes in or near the cochlea.

As above described, our U.S. Pat. No. 4,441,210 describes the tuning of the circuits 30 and 36 to the RF frequency of transmitter 24 and the achieving of critical coupling between the two tuned circuits whereby alignment tolerance of the coils 30 and 36 is increased. However, signal transmission efficiency in such an arrangement is limited to 50%.

In accordance with the present invention the tuned circuits 30 and 36 are detuned whereby closer positioning of the two coils 30, 36 is necessary to achieve optimum coupling. The closer positioning of the coils has the attendant benefit of substantially increasing the signal transmission efficiency while only slightly decreasing the alignment tolerance of the two coils.

FIG. 2 is a plot of transmission efficiency obtained at the relative maximum of the transimpedance over the normalized frequency offset of the transmitter tuned circuit ($x_1$) and the receiver tuned circuit ($x_2$) with respect to the carrier frequency. The plot is actually a three-dimensional surface. From this plot it will be noted that the best efficiency is realized when the receiver tuned circuit is tuned to the carrier frequency (i.e. $x_2=0$), while progressive detuning of the transmitter tuned circuit necessitates increased coupling with the ensuing positive effect of increased efficiency. Experiments have demonstrated that coupling coefficients, K, of up to three are achievable and improved transmission efficiency is achievable.

The following table shows the usable (relative) ranges $\Delta K/K$ of the coupling coefficient, K. K is defined by an allowable drop of the output voltage at the receiver coil of 5% from its maximum value assumed for some value of K within that range. The ensuing relative distance tolerances, $\Delta d/d$, for four different coupling coefficients are as follows:

| K | $x_1$ | $\Delta K/K$ | $\Delta d/d$ |
|---|---|---|---|
| 1 | 0 | 0.67 | 0.58 |
| 1.5 | 1 | 0.58 | 0.36 |
| 2 | 2 | 0.57 | 0.38 |
| 2.5 | 3 | 0.57 | 0.45 |

From this table it is seen that the position tolerance afforded by optimum coupling at $K=1$ is only slightly affected by the detuning to increase efficiency. For example, at $K=1$ the value of $\Delta d/d$ is 0.58; whereas, at $K=2.5$ $\Delta d/d$ is 0.45.

It has been shown that an improved transcutaneous signal transmission system is provided by detuning the transmitter and receiver tuned circuits whereby closer spacing of the coupling coils can be realized for optimum coupling. The closer spacing of the coils permits increased efficiency in signal transmission without significantly affecting alignment tolerance.

While the invention has been described with reference to one embodiment, the description is illustrative of the invention and is not to be construed as limiting the invention. Various modifications and applications may occur to those skilled in the art without departing from the true spirit and scope of the invention as defined by the appended claims.

What is claimed is:

1. In a transcutaneous signal transmission system employing a transmitter coil and a magnetically coupled receiver coil, a method of effeciently transmitting signals while maintaining coil alignment tolerance comprising the steps of
   providing external to a body a transmitter having a first tuned bandpass filter circuit including a first coupling coil, said first tuned circuit being tuned to a first frequency,
   implanting in the body a receiver having a second tuned bandpass filter circuit including a second coupling coil, said second tuned circuit being tuned to a second frequency,
   positioning said first coupling coil with respect to said second coupling coil in a position tolerance range to achieve optimum coupling, and
   transmitting signals between said coupling coils at a third frequency, said third frequency being different from at least one of said first and second frequencies.

2. The method as defined by claim 1 wherein said second frequency and said third frequency are the same.

3. A transcutaneous signal transmission system employing a transmitter coil and a magnetically coupled receiver coil for efficient signal transmission and reception while maintaining coil alignment tolerance comprising
   an external transmitter having a first tuned bandpass filter circuit including a first coupling coil, said first tuned circuit being tuned to a first frequency, and
   an implanted receiver having a second tuned bandpass filter circuit including a second coupling coil, said second tuned circuit being tuned to a second frequency,
   said external transmitter transmitting signals at a third frequency, said third frequency differing from at least one of said first and second frequencies, said first coupling coil being positioned with respect to said second coupling coil to achieve optimum coupling.

4. The transcutaneous signal transmission system as defined by claim 3 wherein said second frequency and said third frequency are the same.

* * * * *